(12) United States Patent
Weintraub

(10) Patent No.: US 11,035,848 B2
(45) Date of Patent: Jun. 15, 2021

(54) SYSTEM AND METHODS FOR IDENTIFYING CANCER CELL LINES HAVING ANTI-GROWTH ACTIVITY AGAINST OTHER CANCER CELL LINES

(71) Applicant: Philip J. Weintraub, New York, NY (US)

(72) Inventor: Philip J. Weintraub, New York, NY (US)

( * ) Notice: Subject to any disclaimer, the term of this patent is extended or adjusted under 35 U.S.C. 154(b) by 0 days.

(21) Appl. No.: 14/561,193

(22) Filed: Dec. 4, 2014

(65) Prior Publication Data

US 2015/0177225 A1 Jun. 25, 2015

Related U.S. Application Data

(60) Provisional application No. 61/920,168, filed on Dec. 23, 2013.

(51) Int. Cl.
*G01N 33/50* (2006.01)
*C12M 1/42* (2006.01)

(52) U.S. Cl.
CPC ......... *G01N 33/5011* (2013.01); *C12M 35/08* (2013.01); *G01N 33/5014* (2013.01); *G01N 33/5044* (2013.01)

(58) Field of Classification Search
None
See application file for complete search history.

(56) References Cited

U.S. PATENT DOCUMENTS

| 8,759,020 B2 | 6/2014 | Wall | |
|---|---|---|---|
| 2006/0135486 A1* | 6/2006 | Owa | A61K 31/36 514/151 |
| 2009/0232382 A1* | 9/2009 | Dioguardi | G06T 7/0012 382/133 |
| 2012/0094325 A1* | 4/2012 | Irimia | B01L 3/502746 435/34 |

FOREIGN PATENT DOCUMENTS

WO 2015099986 A1 7/2015

OTHER PUBLICATIONS

Martine Culty, Mehran Shizari, Erik W. Thompson, and Charles B. Underhill, Binding and degradation of hyaluronan by human breast cancer cell lines expressing different forms of CD44: correlation with invasive potential, 1994, J. Cell. Physiol., vol. 160, pp. 275-286.*

Monks et al., Feasibility of a High-Flux Anticancer Drug Screen Using a Diverse Panel of Cultured Human Tumor Cell Lines, 1991, Journal of the National Cancer Institute, vol. 83, No. 11, pp. 757-766.*

(Continued)

*Primary Examiner* — Michelle F. Paguio Frising
*Assistant Examiner* — Trent R Clarke
(74) *Attorney, Agent, or Firm* — Dentons Durham Jones Pinegar; Sarah W. Matthews

(57) ABSTRACT

The present invention relates to a system and method for identifying malignant cancer cells that produce anti-cancer compounds.

9 Claims, 12 Drawing Sheets

(56) References Cited

OTHER PUBLICATIONS

NPL pdf 'Understanding Your Risk of Developing Secondary Cancers' from the National Comprehensive Cancer Network downloaded from http://www.nccn.org/patients/resources/life_after_cancer/understanding.aspx, published online Aug. 22, 2011 according to Google, accessed Nov. 9, 2015.*
Kirsten Hattermann, Andreas Ludwig, Volkmar Gieselmann, Janka Held-Feindt, Rolf Mentlein, The chemokine CXCL16 induces migration and invasion of glial precursor cells via its receptor CXCR6, 2008, Molecular and Cellular Neuroscience, vol. 39, pp. 133-141.*
Kirsten Hattermann, Janka Held-Feindt, Rolf Mentlein, Spheroid confrontation assay: A simple method to monitor the three-dimensional migration of different cell types in vitro, Annals of Anatomy, vol. 193, pp. 181-184 (Year: 2011).*
W.A. Golembieski, S. Ge, K. Nelson, T. Mikkelsen and S.A. Rempel, Increased SPARC Expression Promotes U87 Glioblastoma Invasion in Vitro, Int. J. Devl. Neuroscience, vol. 17, Nos. 5-6, pp. 463-472 (Year: 1999).*
Maria Wartenberg, Fatma Dönmez, Frederike C. Ling, Helmut Acker, Jürgen Hescheler, and Heinrich Sauer, Tumor-induced angiogenesis studied in confrontation cultures of multicellular tumor spheroids and embryoid bodies grown from pluripotent embryonic stem cells, The FASEB Journal, vol. 15, pp. 995-1005 (Year: 2001).*
Helmut Dolznig, Angelika Walzl, Nina Kramer, Margit Rosner, Pilar Garin-Chesa, Markus Hengstschläger, Organotypic spheroid cultures to study tumor-stroma interaction during cancer development, Drug Discovery Today: Disease Models, vol. 8, No. 2-3, pp. 113-119 (Year: 2011).*
Svein J. T. Nygaard, Hans R. Haugland, Ole Didrik Laerum, Morten Lund-Johansen, Rolf Bjerkvig, and Ole-Björn Tysnes, Dynamic determination of human glioma invasion in vitro, J. Neurosurg., vol. 89, pp. 441-447 (Year: 1998).*
Maria Vinci et al., Advances in establishment and analysis of three-dimensional tumor spheroid-based functional assays for target validation and drug evaluation, BMC Biology, vol. 10, No. 29, pp. 1-20 (Year: 2012).*
N. G. Rainov, S. Koch, M. Sena-Esteves, and M. E. Berens, Characterization of a Canine Glioma Cell Line as Related to Established Experimental Brain Tumor Models, Journal of Neuropathology and Experimental Neurology, vol. 59, No. 7, pp. 607-613 (Year: 2000).*
Douglas Hanahan and Robert A. Weinberg, The Hallmarks of Cancer, Cell, vol. 100, pp. 57-70 (Year: 2000).*
D Oxmann, J Held-Feindt, AM Stark, K Hattermann, T Yoneda and R Mentlein, Endoglin expression in metastatic breast cancer cells enhances their invasive phenotype, 2008, Oncogene, vol. 27, pp. 3567-3575 (Year: 2008).*
NPL pdf document "MDA-MB-231 Cell line profile" was obtained from https://www.phe-culturecollections.org.uk/media/133182/mda-mb-231-cell-line-profile.pdf accessed on Dec. 19, 2020 (Year: 2020).*
M. Nister et al., Evidence for Progressional Changes in the Human Malignant Glioma Line U-343 MGa: Analysis of Karyotype and Expression of Genes Encoding the Subunit Chains of Platelet-derived Growth Factor, 1987, Cancer Research, vol. 47, pp. 4953-4960 (Year: 1987).*
Hua et al, Interactions of Saprophytic Yeasts with a nor Mutant of Aspergillus flavus, 1999 AppJ. Environ. Microbiol 65(6):2738).
Ben-Jacob, Sibling Rivalry in the Bacterial World; available at http://drugdiscoveryopinion.com/2010/03/ibling-rivalry-in-the-bacterialworld/.
Alley et al., Morphometric and Colorimetric Analyses of Human Tumor Cell Line Growth and Drug Sensitivity in Soft Agar Culture; 51 Cancer Research, Feb. 15, 1991, 1247-1256.
Merlo et al., The Role of Genetic Diversity in Cancer; 120 Journal of Clinical Investigation 2010(2):401.
Merlo et al., An in vitro Co-Culture Model of Esophageal Cells Identifies Ascorbic Acid as a Modulator of Cell Competition; BMC Cancer 2011, 11:461.
Earle, Wilton R. et al., The Growth of Pure Strain L Cells in Fluid-Suspension Cultures, Journal of the National Cancer Institute, vol. 14, No. 5, Apr. 1954.
Purves, Dale, Neuronal Competition, Nature vol. 287, Oct. 16, 1980, 585-586.
A. McGehee Harvey, Johns Hopkins—The Birthplace of Tissue Culture: The Story of Ross G. Harrison, Warren H. Lewis, and George O. Gey, The Johns Hopkins Medical Journal 136, 142-149 (1975).
Kuchler, Robert J. and Merchant, Donald J. Growth of Tissue Cells in Suspension, Medical Bulletin, vol. 24 Issue 6, 200-212 (1958).
De La Cova, et al., *Drosophila* Myc Regulates Organ Size by Inducing Cell Competition. Cell, vol. 117, 107-116. Apr. 2, 2004.
Diaz, Begona, and Moreno, Eduardo. The Competitive Nature of Cells. Experimental Cell Research, 306 (2005), 317-322.
Donaldson, Timothy D. and Duronio, Robert J. Cancer Cell Biology: Myc Wins the Competition. Currenty Biology, vol. 14, R425-R427, Jun. 8, 2004.
Gibbings, Derrick J., et al. Multivesicular bodies associate with components of miRNA effector complexes and modulate miRNA activity, Nature Cell Biology, vol. 11 No. 9, Sep. 2009, 1143-1149.
Hanahan, Douglas and Robert Weinberg, The Hallmarks of Cancer. Cell, vol. 100, Jan. 7, 2000, 57-70.
Hanahan, Douglas and Robert Weinberg, Hallmarks of Cancer: The Next Generation, Cell, vol. 144, Mar. 4, 2011, 646-674.
Kandasamy et al., NetPath: a public resource of curated signal transduction pathways. Genome Biology, 2010.
Kosaka et al., Secretory Mechanisms and Intercellular Transfer of MicroRNAs in living cells. The Journal of Biological Chemistry, vol. 285, No. 23, 17442-17452, Jun. 4, 2010.
Kosaka et al. Competitive Interactions of Cancer Cells and Normal Cells via Secretory MicroRNAs. The Journal of Biological Chemistry, vol. 287, No. 2, Jan. 6, 2012.
Parker, Raymond C. Methods of Tissue Culture, Chapter 8: Preparation of Cells and Tissues for Cultivation, 115-137 (Published by Paul B. Hoeber, Inc., New York, Third Edition), published 1950.
Moreno, Eduardo, et al. Cells compete for Decapentaplegic survival factor to prevent apoptosis in *Drosophila* wing development. Nature, vol. 416, Apr. 18, 2002, 755-759.
Moreno, Eduardo, and Basler, Konrad. dMyc Transforms Cells into Super-Competitors. Cell, vol. 117, 117-129, Apr. 2, 2004.
Pegtel, D. Michiel, et al. Functional delivery of viral miRNA via exosomes. PNAS, vol. 107 No. 14, Apr. 6, 2010, 6328-6333.
Rubio-Viqueria, Belen, et al. An in Vivo Platform for Translational Drug Development in Pancreatic Cancer. Clinical Cancer Research, 2006, 12:4652-4661 (Aug. 1, 2006).
Scherer, William F. and Gey, George O. Studies on the Propagation in Vitro of Poliomyelitis Viruses. Viral multiplication in a stable strain of human malignant epithelial cells (strain HeLa) derived from an epidermoid carcinoma of the service (1953). The Journal of Experimental Medicine, vol. 97, pp. 695-710.
Secombe, Julie et al. Myc: A Weapon of Mass Destruction. Cell, vol. 117, 153-156, Apr. 16, 2004.
Weinberg, Robert A. The Biology of Cancer. Garland Science, Taylor & Francis Group, May 2006. Chapter 9: p53 and Apoptosis: Master Guardian and Executioner, p. 342-355.
Abercrombie, M. (1979) Contact Inhibition and Malignancy. Nature, vol. 281, 259-262.
Written Opinion of the International Searching Authority from related PCT App. No. 2014/068896, dated Mar. 9, 2015.
International Search Report from related PCT App. No. 2014/068896, dated Mar. 9, 2015.
Yasuhiro Miki et al.: "The advantages of co-culture over mono cell culture in simulating environment," Journal of Steroid Biochemistry and Molecular Biology, Elsevier Science Ltd., Oxford, GB, vol. 131, No. 3, Dec. 11, 2011, pp. 68-75, XP028498105, Abst. only.
J.T. Camp et al.: "Interactions with fibroblasts are distinct in basal-like and luminal breast cancers," Molecular Cancer Research, vol. 9, No. 1, Dec. 3, 2010, pp. 3-13, XP055171292.

(56) References Cited

OTHER PUBLICATIONS

Liyuan Li et al.: "Optimizing a 3D culture system to study the interaction between epithelial breast cancer and its surrounding fibroblasts," Journal of Cancer, vol. 203221725, Jan. 1, 2011, p. 458, XP055171866.

Stefanie Loffek et al.: "High invasive melanoma cells induce matrix metalloproteinase-1 synthesis in fibroblasts by interleukin-1a and basic fibroblast growth factor-mediated mechanisms," Jan. 1, 2005, XP55171904.

Nina Kramer et al.: "In vitro cell migration and invasion assays," Mutation Research/Reviews in Mutation Research, vol. 752, No. 1, Jan. 1, 2013, pp. 10-24, XP055172218, Abst. only.

Quail et al.: "A unique 3D in vitro cellular invasion assay." Journal of Biomolecular Screening Society for Laboratory Automation and Screening, Jan. 1, 2012, pp. 1088-1095, XP055172308.

A. P. Vamvakidou et al.: "Heterogeneous breast tumoroids: an in vitro assay for investigating cellular heterogeneity and Drug delivery," Journal of Biomolecular Screening, vol. 12, No. 1, Nov. 12, 2006, pp. 13-20, XP055172501.

International Preliminary Report on Patentability from related PCT App. No. 2014/068896, dated Jun. 28, 2016.

Weintraub, Philip, "Quantification of tumor virulence based upon competition between dissimilar subcultured cancer cell lines," International Journal of Surgery Oncology, Experimental Research, Jan. 19, 2021, 6 pages.

\* cited by examiner

MICROSCOPING ANALYSIS

BRIDGING OVER

CHANNELING THROUGH

TUNNELING UNDER

LADDERING UP

MICROSCOPIC SCORING SYSTEM

MOST OFFENSIVE                         POINTS

| | |
|---|---|
| BRIDGING | +4 PER BRIDGE |
| TUNNELING | +3 PER TUNNEL |
| CHANNELING | +2 PER CHANNEL |
| LADDERING | +1 PER CLUMP |
| LOSS OF CELL CONTACT | -1 PER CELL |
| CELL CLUMPING | -2 PER CLUMP |
| CELL NECROSIS | -3 PER CLUSTER |
| CELL CRATERS | -4 PER CRATER |

MOST DEFENSIVE

SYSTEM AND METHODS FOR IDENTIFYING CANCER CELL LINES HAVING ANTI-GROWTH ACTIVITY AGAINST OTHER CANCER CELL LINES

FIELD OF THE INVENTION

The present invention relates to systems and methods for identifying anti-cancer compounds produced by malignant cancer cells.

BACKGROUND

Cancer cells are unlike normal cells in that they manifest sustained proliferative signaling, evade growth suppressors, activate invasion and metastasis, enable replicative immortality, induce angiogenesis, resist cell death, and do not manifest inter-cellular contact inhibition. Each of these characteristics contributes to the difficulty of developing anti-cancer treatments.

Inter- and intra-cellular communication is generally thought to play a central role in the process of malignant transformation and carcinogenesis. The biochemical responses of cells to stimuli in their extra-cellular microenvironment generally regulate the intricate biological processes of proliferation, migration and apoptosis. Apoptosis, originally termed programmed cell death, is physiologically distinct and morphologically differentiated from necrotic cell death (Lockshin, 1965). Necrotic cell death, with consequent release of cellular contents into the extracellular medium that potentially endangers surrounding cells, follows cellular injury and inflammatory swelling, loss of membrane integrity, and cellular lysis. In contrast, apoptosis does not include the inflammatory response, and is characterized by blebbing of the cell membrane, reduction in cellular dimension, condensed chromatin, and DNA that becomes fragmented. Macrophages or neighboring cells may ultimately engulf the apoptotic cell (Kerr, 1972).

Binding of extracellular ligands to cell-surface receptors results in the initiation of sequences of intracellular responses, known as signal transduction pathways. Intracellular communication pathways utilize large protein complexes as effector molecules in signaling cascades. Signals from one source are processed and passed on to another, downstream intra-cellular protein during intra-cellular signal transduction. A substantial proportion of pathologic phenotypes of cancer cells are believed to result from aberrantly functioning intracellular signal-transduction molecules (Weinberg 2006; Kandasamy 2010; Hannahan 2011).

The ability to sustain chronic proliferation is one of the most fundamental traits known to exist in cancer cells. Under normal conditions, homeostasis of cell number and thus maintenance of normal tissue architecture and function is preserved by the precise regulation of growth-promoting production and release signals that instruct entry into and progression through the cell growth and-division cycle. Cancer cells become independent of these homeostatic controls by deregulation of extra-cellular signals, which are typically mediated by growth factors that interact with cell-surface receptors that typically contain intracellular tyrosine kinase domains. Subsequently, intracellular signals are generated from the tyrosine kinase domains, and propagating via branched intracellular signaling pathways, regulate cell cycle progression, cell growth, survival and energy metabolism. Presently, the nature of proliferative signals that function within normal tissues remain poorly characterized. Additionally, comparatively little insight exists into the mechanisms controlling cellular proliferation and the release of mitogenic signals (Weinberg 2006).

The growth factor signaling pathways that regulate cell number and position within tissues are difficult to access experimentally. These extra-cellular communications are transmitted through paracrine signaling in the pericellular and extracellular matrix between cells, controlled by a complex network of proteases, sulfatases, and other enzymes that liberate and activate them in a temporally and spatially regulated manner which has limited the precise elucidation of these extra-cellular mechanisms.

On the other hand, greater insight has been acquired into intra-cellular mitogenic signaling (Lemmon and Schlessinger, 2010; Witsch et al., 2010; Hynes and MacDonald, 2009; Perona, 2006). Sustained proliferative signaling in cancer cells may develop in several ways. Autocrine proliferative stimulation may result in cancer cells via the expression of cognate receptors to growth factor ligands which they have produced. Also, normal cells within the supporting tumor-associated stroma may supply cancer cells with various growth factors in response to signals they have received from them (Cheng et al., 2008; Bhowmick et al., 2004). Sustained proliferative signaling in cancer cells may also result from hyper-responsiveness to available growth factor ligands secondary to increased levels of receptor proteins produced on the surface of the cancer cell. Structural alterations in the receptor molecules that enable ligand-independent activation may also contribute to sustained proliferative signaling. Additionally, constitutive activation of signaling pathway components operating downstream of cell surface receptors may also culminate in growth factor independence, eliminating the necessity to re-stimulate these pathways by ligand-mediated receptor activation. However, since multiple downstream signaling pathways may emanate from a single ligand-stimulated receptor, the activation of a specific downstream pathway, such as the pathway responding to the Ras signal transducer, may only represent a subset of the aggregate regulatory instructions signaled by cell surface receptor activation (Weinberg 2006).

Thus, there appear to be numerous mechanisms by which diverse tumor cell types can coexist, predominate or dominate when competing for the same pool of resources, and there is, accordingly, a need to elucidate the mechanisms and inter-cellular processes responsible for mitogenic and proliferative signaling, apoptotic resistance, evasion of growth suppressors, and replicative immortality, and to identify and utilize compounds responsible for such cellular processes in order to identify compounds having anti-cancer activity.

SUMMARY OF THE INVENTION

The present invention relates to improved systems and methods for identifying anti-cancer compounds. More particularly, the present invention relates to systems and methods for identifying and cultivating effective and specific treatment against cancer by harnessing the ability of sub-cultured cancer cells, which when forced to compete with a second cancer in a limited and challenging in vitro environment, will exhibit superiority over the second cancer through the expression of an arsenal of proteins and polypeptides. Such proteins and polypeptides can then be isolated, purified, and further characterized to provide potential anti-cancer compounds for use in treating the cancer against which the proteins and polypeptides were effective in combating in vitro.

The present invention provides a method for identifying malignant cancer cells that produce anti-cancer compounds by culturing malignant cancer cells of different types in a confrontation. In one embodiment, the method comprises the following steps:

plating on a culture plate in a growth medium a colony of first malignant cancer cells and a colony of second malignant cancer cells on directly opposite sides of a midline adjacent one another, wherein the colony of first malignant cancer cells and the colony of second malignant cancer cells are of different cancer types;

culturing the colony of first malignant cancer cells and the colony of second malignant cancer cells under conditions sufficient to promote growth of the cancer cells and permit one of the colony of first malignant cancer cells and the colony of second malignant cancer cells to display dominant properties relative to the other; and selecting from one of the colony of first malignant cancer cells and the colony of second malignant cancer cells dominant malignant cancer cells that display dominant properties relative to the other that are indicative of anti-cancer properties, wherein the dominant malignant cancer cells produce compounds having anti-cancer properties against the other colony of malignant cancer cells.

In another aspect, the invention provides a cell culture system for identifying malignant cancer cells that produce anti-cancer compounds, comprising a culture plate comprising a growth medium capable of promoting the growth of a first colony of malignant cancer cells and a second colony of malignant cancer cells, wherein the first colony of malignant cancer cells and the second colony of malignant cancer cells are plated on the culture plate on directly opposite sides of a midline adjacent to one another under culture conditions sufficient to promote the competitive growth of the first colony of malignant cancer cells and the second colony of malignant cancer cells, wherein the first colony of malignant cancer cells and the second colony of malignant cancer cells are of different cancer types.

In yet another embodiment, the methods of the present invention may further comprise the following steps:

plating on a culture plate in a growth medium a third colony of malignant cancer cells and a fourth colony of cancer cells adjacent to and on opposite sides of a midline, wherein the first colony of malignant cancer cells, the second colony of cancer cells, the third colony of cancer cells and the fourth colony of cancer cells are of different cancer types;

culturing the colony of third malignant cancer cells and the colony of fourth malignant cancer cells for a period of time and under conditions sufficient to allow the colony of third malignant cancer cells and the colony of fourth malignant cancer cells to compete against each other;

selecting from one of the colony of third malignant cancer cells and colony of fourth malignant cancer cells a second colony of dominant malignant cancer cells that display anti-cancer properties;

plating on a culture plate in a growth medium the colony of first dominant malignant cancer cells and the colony of second dominant malignant cancer cells for a period of time and under conditions sufficient to allow the colony of first dominant malignant cancer cells and the colony of second dominant malignant cancer cells to compete against each other; and selecting from the colony of first dominant malignant cancer cells and the colony of second set of dominant malignant cancer cells super dominant malignant cancer cells that display dominant properties as between the first set of dominant malignant cancer cells and the second set of dominant malignant cancer cells.

These and other aspects of the present invention are realized as shown and described in the following figures and related description. It is further understood the the claims, which described additional embodiments, shall be considered part of the disclosure of the present invention. It will be appreciated that various embodiments of the invention may not include each aspect set forth above and aspects discussed above shall not be read into the claims unless specifically described therein.

BRIEF DESCRIPTION OF THE DRAWINGS

Various embodiments of the present invention are shown and described in reference to the numbered drawings wherein.

Figure 1:
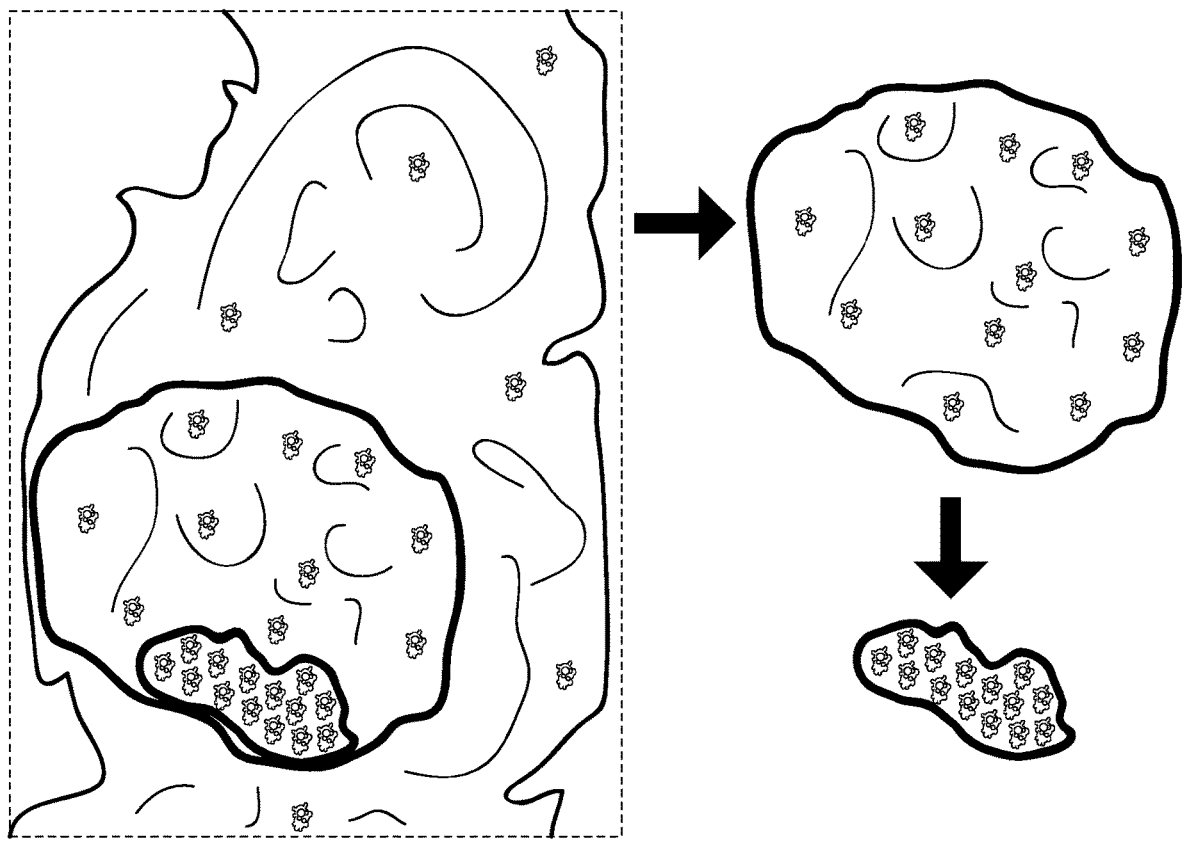
FIG. 1 illustrates the selection of a group of cancer cells from a tumor.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The skilled artisan will understand, however, that the apparatuses, systems and methods described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Definitions

Reference in the specification to "one embodiment" or "an embodiment" means that a particular feature, structure, or characteristic described in connection with the embodiment is included in at least one embodiment, but is not a requirement that such feature, structure or characteristic be present in any particular embodiment unless expressly set forth in the claims as being present. The appearances of the phrase "in one embodiment" in various places may not necessarily limit the inclusion of a particular element of the invention to a single embodiment, rather the element may be included in other or all embodiments discussed herein.

Furthermore, the described features, structures, or characteristics of embodiments of the invention may be combined in any suitable manner in one or more embodiments. In the following description, numerous specific details are provided, such as examples of products or manufacturing techniques that may be used, to provide a thorough understanding of embodiments of the invention. One skilled in the relevant art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinarily skill in the relevant art. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, reference to "a spring" may include one or more of such springs, and reference to "the layer" may include reference to one or more of such layers.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Description of Embodiments

The systems and methods of the present invention are illustrated by the following detailed description of specific embodiments of the invention and experimental results.

In one aspect, the present invention provides a method for identifying malignant cancer cells that produce anti-cancer compounds by culturing malignant cancer cells of different types in a confrontation on a culture plate. In one embodiment, for example, such a confrontation may comprise the steps of plating on a culture plate in a growth medium a colony of first malignant cancer cells and a colony of second malignant cancer cells on directly opposite sides of a midline adjacent one another, wherein the colony of first malignant cancer cells and the colony of second malignant cancer cells are of different cancer types. The colony of first malignant cancer cells and the colony of second malignant cancer cells are then cultured under conditions sufficient to promote growth of the cancer cells and permit one of the colony of first malignant cancer cells and the colony of second malignant cancer cells to display dominant properties relative to the other. After the above culturing step, from one of the colony of first malignant cancer cells and the colony of second malignant cancer cells are selected dominant malignant cancer cells that display dominant properties relative to the other that are indicative of anti-cancer properties, wherein the dominant malignant cancer cells produce compounds having anti-cancer properties against the other colony of malignant cancer cells.

As used herein, the term "midline," refers to an imaginary or marked line on a culture plate. The midline is essentially a boundary line, on one side of which is plated a colony of first malignant cancer cells and on the other side of which is plated a colony of second malignant cancer cells. In some embodiments the midline is a straight line or a substantially straight line. In other embodiments, the midline may be a curved or irregular line. The midline may be positioned at any location on the culture plate, for example, in the middle of the culture plate, or off center of the culture plate, provided sufficient space is provided around the first malignant cancer cells and the second malignant cancer cells to allow for expansion of the cancer cells, preferably without reaching the outermost edge of the culture plate. The term "midline" does not, therefore imply or connote that the line is necessarily positioned at a precise midpoint on the culture plate. Rather, the midline is merely a reference point between two distinct colonies of malignant cancer cells that are positioned for growth confrontation.

The term "adjacent", as used herein in reference to a first colony of malignant cells being "adjacent" to a second colony of malignant cells, means that the respective cells are sufficiently close in proximity that the cellular components expressed by one colony of malignant cells is capable of interacting with or influencing the other colony of malignant cells. In some embodiments, the cells on the edge of the first colony are sufficiently close that they tough touch the cells of the second colony. In other embodiments, the cells of the first colony may not actually touch the cells of the second colony, but are sufficiently close that the extracellular components produced by the first colony and second colony migrate to and influence the growth of cells in the other colony.

The term "directly opposite," as used herein in reference to a first colony of malignant cells being "directly opposite" a second colony of malignant cells means that the first colony of malignant cells and the second colony of malignant cells are positioned across from each other on opposite sides of the midline.

In another aspect of the invention, the cancer cells used in the above confrontation may be derived from a single source. For example, in one particular embodiment, the colony of first malignant cancer cells and the colony of second malignant cancer cells are each derived from a homogeneous subculture of malignant cancer cells. Likewise, in another embodiment, each of the colony of first malignant cancer cells and the colony of second malignant cancer cells may also each be derived from a different single malignant cancer cell.

In one embodiment, the colony of first malignant cancer cells and the colony of second malignant cancer cells plated each have substantially an equal number of cancer cells. In some embodiments, the colony of first malignant cancer cells and the colony of second malignant cancer cells plated each have about $10^4$ cells or greater. In other embodiments, the colony of first malignant cancer cells and the colony of second malignant cancer cells plated each have about $10^5$ cells or greater. In yet other embodiments, the colony of first malignant cancer cells and the colony of second malignant cancer cells plated each have about $10^5$ cells or greater. It is understood that the first and second colonies of cancer cells need not have exactly the same number of cells, but that the closer the number of cells in each group the easier it will be to make a comparison of which colony of cancer cells is dominant, based on the number of cancer cells remaining in each colony. If a different number of cancer cells is used for the first and second colonies of cancer cells, it may be possible, for example, to normalize the data so as to obtain statistically significant results, notwithstanding the difference in the number of cells.

In another aspect of the invention, the area over which the first and second colony of malignant cancer cells is plated is selected such that the relative differences in growth over the course of culturing can be readily ascertained. For example, in some embodiments, the colony of first malignant cancer cells and the colony of second malignant cancer cells plated each cover an area that is substantially equal. Plating about an equal number of cells, plated over about an equal area, generally simplifies the comparison of territorial expansion or regression, without the need to normalize the data for purposes of determining which cell line is expanding or regressing.

In another aspect of the invention, the confrontation between two different malignant cells types may be performed in multiple steps, for example, with a first confrontation that identifies a dominant malignant cell type, followed by a second confrontation using the dominant malignant cell type identified in the first confrontation. Similarly, the methods of the invention may also comprise the step of subculturing and expanding the selected dominant malignant cancer cells.

In another aspect, the present invention may further include means for quantitating the extent or degree of dominant behavior associated with territorial expansion of a dominant cell type. For example, in one embodiment the culture plate may comprise unit markers for scoring the area of expansion of the dominant malignant cancer cells. Such unit markers may be in either standard U.S. measurement units (such as inches) or metric units (cm). The unit markers may comprise vertical and/or horizontal line markers, marked to enable visibility and measurement of the area of expansion of a dominant cell type (or area of regression of a submissive cell type).

In some aspects, the present invention provides criteria for ascertaining and quantitating dominance of a cell type. For example, in some embodiments the dominant malignant cancer cells are scored on the basis of a change of the dominant malignant cancer cells. In some particular embodiments, such a change is selected from one or more of the properties of increased size, reddish color, firmness of texture and area of expansion across the culture plate due to cellular growth. In other embodiments, the dominant malignant cancer cells may also be scored on the basis of a change of submissive malignant cancer cells near the dominant malignant cancer cells. For example, the submissive malignant cancer cells may be scored on the basis of change of the submissive malignant cancer cells, wherein the change is selected from one or more of decreased size, bluish color, soft texture, and area of contraction due to cellular death.

In another embodiment, the dominant malignant cancer cells may be scored on the basis of relative dominant properties. Some dominant properties, for example, may be more indicative of the presence of an anti-cancer compound than other dominant properties. In particular, in some embodiments, the dominant property of bridging over (growing upwardly in the culture dish and over onto the other colony) is given greater relative weight than the dominant property of tunneling under (growing between the other colony and its agar base layer). In other embodiments, the dominant property of tunneling is given greater relative weight than the dominant property of channeling (growing directly through the middle). In yet other embodiments, the dominant property of channeling is given greater relative weight than the dominant property of laddering up (growing upwardly or vertically).

Similarly, the submissive malignant cancer cells may be scored on the basis of relative submissive properties. In some embodiments, the submissive property of cell clumping (aggregating together to form a more dense or segregated group of cells) is given greater relative weight than the submissive property of loss of cell contact (where cells may disaggregate and form single cells or smaller groups of cells). In other embodiments, the submissive property of cell clumping is given greater relative weight than the submissive property of cell necrosis (death of cells). In yet other embodiments, the submissive property of cell necrosis is given greater relative weight than the submissive property of cell craters (regions where cells do not grow).

In another aspect, the present invention provides methods in which a dominant cell type is identified in a first confrontation, and then that same dominant cell type is matched against a third cell type in a second confrontation. For example, in one embodiment, the methods may include the step of culturing the colony of dominant malignant cancer cells with a colony of second dominant malignant cancer cells selected from a second confrontation performed in accordance with the same method.

In another aspect, the present invention also contemplates that following the confrontation(s) and identification of a dominant malignant cell type, the dominant malignant cancer cells will be separated from the extracellular components and the extracellular components will be analyzed to identify an extracellular component responsible for the dominant properties of the malignant cancer cells. Such separation techniques are well known to those skilled in the art, and include, for example, precipitation methods based on solubility of proteins (using ammonium sulfate, or polyethylene glycol). Various chromatography methods are also available that separate proteins on the basis of net charge (such as ion-exchange methods that separate anions and cations), surface hydrophobicity (hydrophobic interaction), metal binding sits (metal affinity), ligand binding sites (ligand affinity, e.g., NAD or NADP), subunit/oligome size or shape (gel filtration). Proteins may also be separated based on size or shape using centrifugation. Separation of proteins to obtain purified proteins having a particular anti-cancer activity is generally accomplished by the following steps: (1) extracting the proteins from various other biological materials (such as cell walls, etc.), (2) separating the protein containing portion from the non-protein components (nucleic acids and lipids), (3) precipitating the desired protein fraction, initially to recover the bulk protein from a crude extract, followed by preliminary resolution into manageable fractions; (4) separating the target protein-containing fraction from the bulk protein by using ion-exchange chromatography/size fractionation or hydrophobic chromatography columns; and (5) a final refining step of, which may include an "affinity" matrix to enable recovery of the target protein in a highly purified state along with a high yield. A variety of agarose-based matrices with immobilized reactive dyes, covalently bound nucleotides, metals and numerous other ligands are commercially available from such sources as Sigma, Amicon, etc.

In order to evaluate the progress of purification, a convenient assay procedure—based on enzymatic activity or some other easily monitored property specific to the protein—should be available. A spectrophotometric or colorimetric method for enzymatic activity measurement is most convenient and a progressive increase in specific activity (for enzymes, activity in units/mg protein) is an excellent indicator of the efficacy of the purification step. For proteins lacking a readily measurable biological activity, it may be feasible to use an immunochemical procedure such as western blotting or ELISA (Enzyme-Linked-Immuno-sorbent Assay), provided suitable antibodies are available. In this case, electrophoretic resolution of the protein population in samples at each stage of purification will be required.

In some embodiments, the methods of the invention may include the step of analyzing the extracellular components to identify an extracellular component responsible for the dominant properties of the malignant cancer cells comprises separating the extracellular components by size and testing components of similar size for anti-cancer activity. Anti-cancer activity is identified in fractions containing the anti-cancer compounds by taking a portion of a fraction and testing it in an assay that detects such anti-cancer activity.

In another aspect, the methods of the present invention may also include plating the two different malignant cell types such that the cell types are plated along the midline in a substantially balanced orientation. For example, in some embodiments, the colony of first malignant cancer cells and the colony of second malignant cancer cells are plated on the culture plate at an intermediate point of the midline, wherein a portion of the colony of first malignant cancer cells and a similarly sized portion of the colony of second malignant cancer cells are plated on one side of the intermediate point of the midline, and the remaining portion of the colony of first malignant cancer cells and a similarly sized remaining portion of the colony of second malignant cancer cells are plated on the other side of the intermediate point of the midline. In some particular embodiments, for example, the intermediate point is from about 25% to about 75% of the distance along the midline. In other particular embodiments, the intermediate point is at about the center point of the midline. In yet other embodiments, the portion of the colony of first malignant cancer cells represents about 50% of the colony of first malignant cancer cells and the similarly sized portion of the colony of second malignant cancer cells represents about 50% of the colony of second malignant cancer cells. In yet another embodiment, the colony of first malignant cancer cells and the colony of second malignant cancer cells are plated directly opposite one another on opposite sides of the midline, and are positioned on the midline such that there is sufficient room between the plated cells and the edge of the culture dish that the cancer cells may expand beyond the side edges of the plated cells. Of course, by plating the cells in a central region of the culture dish, the area between the cells and the edge of the culture dish is maximized.

In accordance with the principles described herein, in some embodiments the colony of first malignant cancer cells and the colony of second malignant cancer cells are cultured for a period of time and under conditions sufficient to allow the colony of first malignant cancer cells and the colony of second malignant cancer cells to compete against each other. In such competition, it was discovered that some malignant cell types will display dominant properties relative to the other malignant cell line in such a confrontation.

In some embodiments, it is contemplated that a sufficient number of malignant cancer cells will be plated so as to enable the cells to take on the characteristics of a colony that would be present in vivo in a patient having cancer. For example, in some embodiments, the colony of first malignant cancer cells and the colony of second malignant cancer cells are plated at a density of about $10^6$ cells/mL or greater, or, in other embodiments, at a density of about $10^5$ cells/mL or greater, or, in other embodiments, at a density of about $10^4$ cells/mL or greater.

As suggested above, the present invention also contemplates that multiple rounds of confrontations in order to identify a super dominant cell type that is relatively more dominant than various other cell types. For example, in some embodiments, the present invention may also include the steps of plating on a culture plate in a growth medium a third colony of malignant cancer cells and a fourth colony of cancer cells adjacent to and on opposite sides of a midline, wherein the first colony of malignant cancer cells, the second colony of cancer cells, the third colony of cancer cells and the fourth colony of cancer cells are of different cancer types. The colony of third malignant cancer cells and the colony of fourth malignant cancer cells are then cultured for a period of time and under conditions sufficient to allow the colony of third malignant cancer cells and the colony of fourth malignant cancer cells to compete against each other. After the cells are cultured in the above confrontation, from one of the colony of third malignant cancer cells and colony of fourth malignant cancer cells is selected a second colony of dominant malignant cancer cells that display anti-cancer properties. The colony of first dominant malignant cancer cells and the colony of second dominant malignant cancer cells is then plated on a culture plate in a growth medium for a period of time and under conditions sufficient to allow the colony of first dominant malignant cancer cells and the colony of second dominant malignant cancer cells to compete against each other. From the colony of first dominant malignant cancer cells and the colony of second set of dominant malignant cancer cells is then selected a super dominant malignant cancer cells that display dominant properties as between the first set of dominant malignant cancer cells and the second set of dominant malignant cancer cells. As described in more detail above, the extracellular components that contain anti-cancer compounds is then separated from the super dominant malignant cancer cells, and anti-cancer compound is isolated from the extracellular components.

In another aspect, the present invention also provides a cell culture system for identifying malignant cancer cells that produce anti-cancer compounds, comprising a culture plate comprising a growth medium capable of promoting the growth of a first colony of malignant cancer cells and a second colony of malignant cancer cells, wherein the first colony of malignant cancer cells and the second colony of malignant cancer cells are plated on the culture plate on directly opposite sides of a midline adjacent to one another under culture conditions sufficient to promote the competitive growth of the first colony of malignant cancer cells and the second colony of malignant cancer cells, wherein the first colony of malignant cancer cells and the second colony of malignant cancer cells are of different cancer types.

The following provides a general description of one possible embodiment of the present invention. It is understood that the particular conditions and steps described below are not the only way in which the methods of the invention may be practiced. Those skilled in the art will readily appreciate that the reagents and conditions can be modified and that alternative reagents and cell culture conditions may be used as appropriate for particular cells lines being used.

The methods of the present invention utilize the properties of cancer cells found in tumors obtained from a patient. Such cancer cells may, for example, be procured by surgically excising the cells from a patient and pathologically confirming that the cells are malignant and suitable for use in the methods described herein. The selection of malignant cancer cells may, for example, be accomplished by gross examination of specimens to identify neighborhoods of neoplasia that are most likely to contain the highest density of cancer cells and harvesting the cells by excising them from the surrounding tissue, as shown in FIG. 1.

After selecting an appropriate colony of cancer cells and harvesting them from a cancer-rich neighborhood, the cells can then be delicately transferred to a receiver flask. The cells are then washed in a well-balanced salt solution to remove impurities and to preserve viability. The cancer cells are then dissociated with trypsin to produce a cell suspension. The suspension of cancer cells is then examined, for example, with use of a Coulter counter, to determine the percentage of dissociation and viability of the cells. Ideally, a suspension of cells that is greater than 90% dissociated and viable is desired. If the cells are less than about 90% dissociated, but greater than 90% viable, the steps above steps should be repeated, beginning with the step of dissociating the cancer cells with trypsin, until a suspension of cells is obtained that is greater than 90% dissociated and viable. Similarly, if the cells are less than 90% viable, the contents should be discarded and the process should be started again with the harvesting step described above.

Once a suitable suspension of cells is obtained, as described above, the suspension of cancer cells is then diluted with an appropriate medium, such as McCoys medium 5A supplement with a 5% fetal calf serum solution, to achieve a concentration of, for example, about 100,000 cells/mL. About 10 mL of the cancer cell suspension is then subcultured on a bed of pre-warmed growth medium to be deposited into an incubated tumor bank for future use.

The tumor bank can then be expanded by selecting and harvesting other tumors types from a new and freshly diagnosed malignant solid tumor and preparing a suitable tumor bank using the above steps. For purposes of such an experimental study, it is desirable, though not necessary, to obtain about 10 different stock tumor accounts. These additional tumor cell preparations can then be used in an experimental system where a first tumor cell preparation is used to challenge a second tumor cell preparation, a third tumor cell preparation, a fourth tumor cell preparation, and so forth, to determine which of the tumor cell preparations may be effective in challenging the first tumor cell preparation. One skilled in the art will appreciate that the various combinations of the tumor cell preparations are possible, in order to identify which tumor cell preparations are effective in challenging any one of the other tumor cell preparations.

Figure 2:
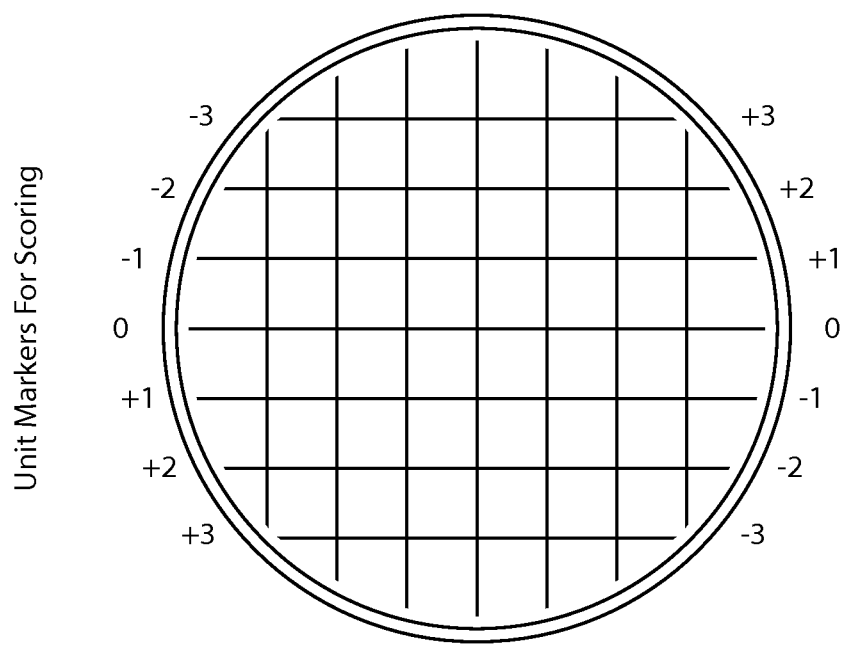
FIG. 2 shows a gridded culture dish.
Figure 3:
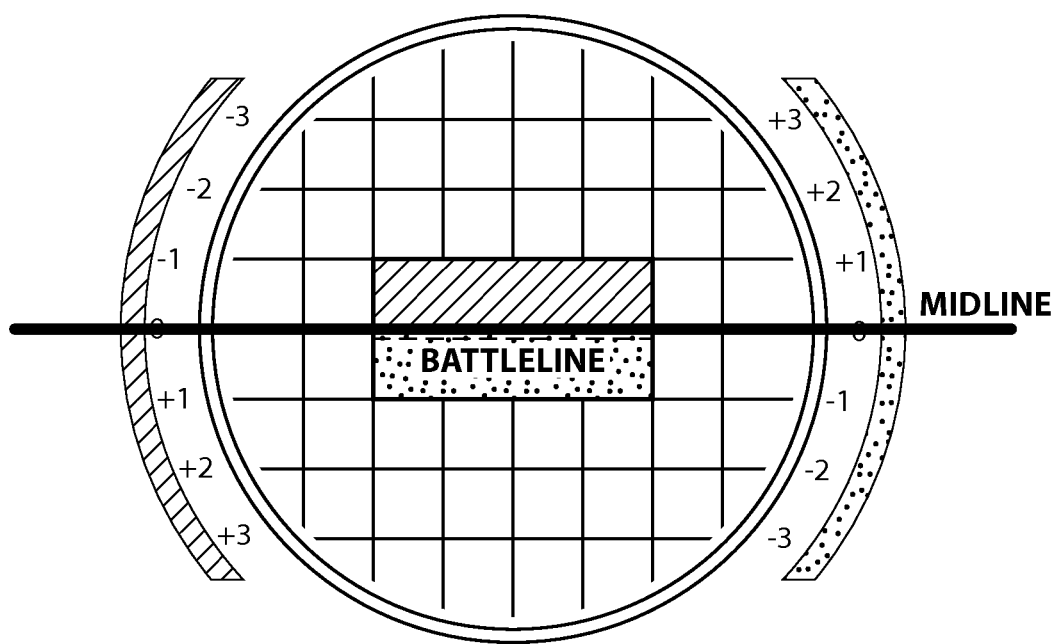
FIG. 3 shows a culture dish with cancer cells from a stock tumor account (diagonal hatched lines region) plated against cancer cells of a target tumor (dotted region) on respective sides of a battleline (midline).

In one embodiment, the tumor cell challenges may be implemented, for example, by the process described below. First a battle dish is prepared, which comprises a gridded petri dish, filled with enriched growth medium, as shown in FIG. 2. The unit markers on the battle dish provide a quantitative measure of the extent to which one tumor cell population is effective in expanding into the territory of a competing tumor cell population. A suitable number of cancer cells from the stock tumor accounts are plated against a similar number of the target tumor. It is understood that the precise number is not critical, but a sufficient number should be selected to allow the the stock tumor cells and the target tumor cells to effectively grow under the culture conditions and be influenced by the other group of cells. In one particular embodiment, for example, approximately 100,000 cancer cells are withdrawn from each of 10 established stock tumor accounts and are plated against 100,000 cancer cells of the target tumor in 12 different battle dishes on equal but opposing areas along the battleline, such as a midline of the battle dish, as shown in FIG. 3. The stock tumor (shown as region indicated by diagonal hatched lines in FIG. 3) is incubated adjacent to the target tumor (shown as dotted region in FIG. 3) in the battle dish under standard conditions sufficient to allow both the stock tumor and the target tumor to grow, for example, at 37° C. for 7 days with a humidified atmosphere of 5% $CO_2$. After the incubation period is complete, each of the 10 battle dishes from the incubator is removed and the medium is examined, paying particular attention to changes in size, color, texture and movement across the battle dish.

The extent to which one tumor cell population has effectively suppressed the other tumor cell population is then determined. Various methods available in the art are available to quantitatively determined the expansion (or diminution) of a cell population. For example, digital methods may be used to measure the total area of a first population of cancer cells and compare it with the total area of a second population of cancer cells. Similarly, methods may be used for awarding pre-determined points to both the target tumor and the stock tumor for aggressive behaviors and reciprocally subtracting points for passive and submissive behaviors, as described below in Table 1.

TABLE 1

Scoring System for Aggressive and Passive Responses to Cell Challenge

| Size | Increased | Unchanged | Decreased | |
|---|---|---|---|---|
| | Small +1 | 0 | Small −1 | |
| | Medium +2 | 0 | Medium −2 | |
| | Large +3 | 0 | Large −3 | |
| Color | Redish Hue | Unchanged | Blueish Hue | |
| | Small +1 | 0 | Small −1 | |
| | Medium +2 | 0 | Medium −2 | |
| | Large +3 | 0 | Large −3 | |
| Texture | Firm | Spongy | Soft | Soggy |
| Motion | +2 Partial penetration | +1 Full penetration | −1 Movement across midline without direct contact | −2 Lateral movement |

Figure 4:
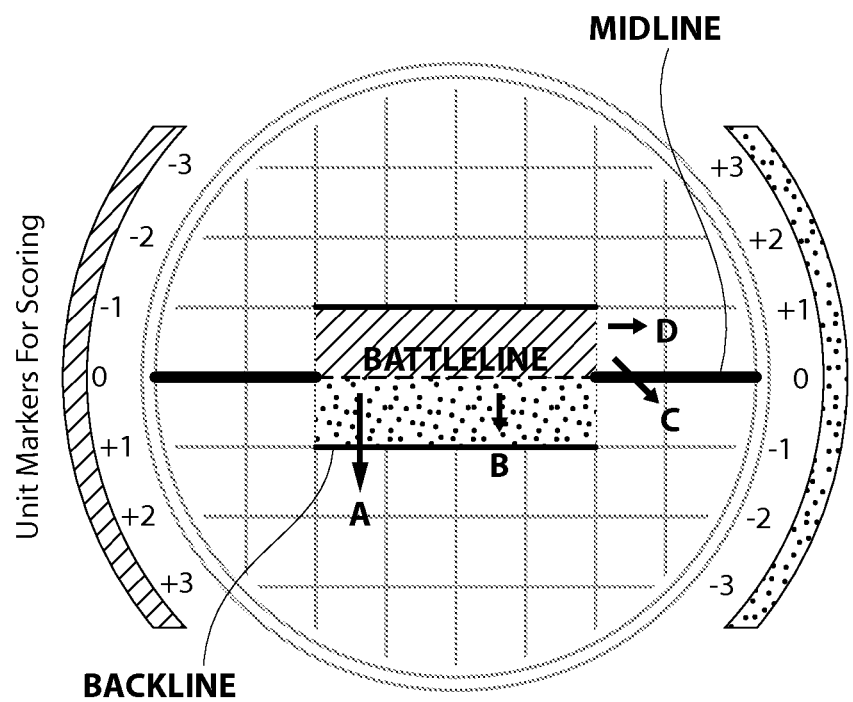
FIG. 4 shows a culture dish, illustrating various offensive behaviors of a dominant cancer cell line (diagonal hatched lines region).

FIG. 4 illustrates the following various types of offensive characteristics or "maneuvers" that may be displayed by a dominant tumor cell population.

A. Penetration through both the battleline and backline.
B. Penetration through the battleline but not beyond the backline.
C. Movement across the midline without direct contact with the battleline or the backline.
D. Lateral movement without contact with the battleline or the backline. Table 2, below, illustrates a possible scoring system for specific offensive maneuvers described in FIG. 4.

TABLE 2

Offensive Maneuvers

| A | B | C | B |
|---|---|---|---|
| +4 Plus Each Unit Marker Surpassed | +3 | +2 | +1 |

Figure 5:
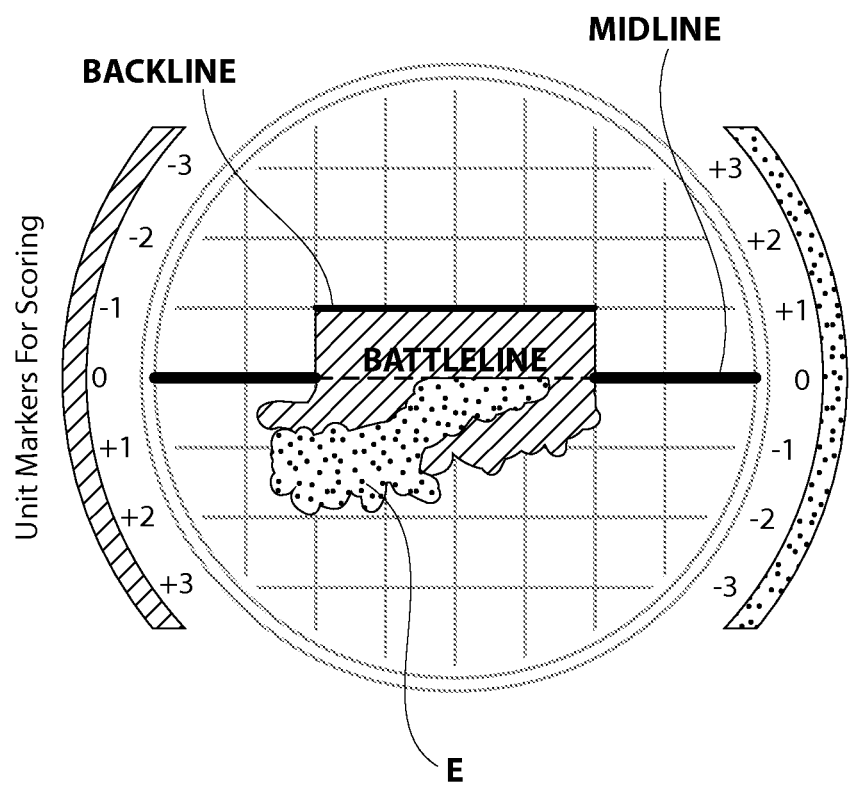
FIG. 5 shows a culture dish, illustrating various offensive behaviors of a dominant cancer cell line (diagonal hatched lines region) expanding into another cancer cell line territory (dotted region), and also illustrating a defensive behavior of a cancer cell line (dotted region) partially retreating behind a backline.
Figure 6:
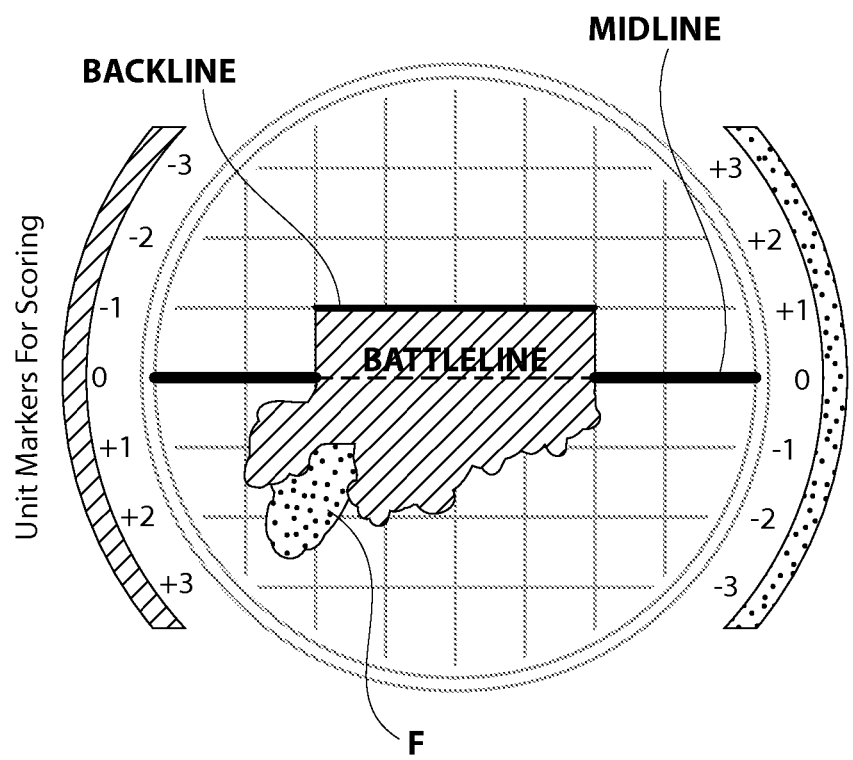
FIG. 6 shows a culture dish, illustrating a defensive behavior of a cancer cell line (dotted region) fully retreating behind a backline.

Similarly, FIGS. 5 and 6 illustrate the following various types of defensive characteristics or "maneuvers" that may be displayed by a subservient or submissive tumor cell population that is dominated by another tumor cell population:

E. Partial withdrawal from the battleline through the backline, as shown in FIG. 5 (with a possible scoring system shown in Table 3, below)

TABLE 3

Defensive Maneuvers
E

−3 Minus Each Unit Marker Surpassed

F. Full retreat from the battleline, as shown in FIG. 6 (with a possible scoring system shown in Table 4, below).

TABLE 4

Defensive Maneuvers
F

−4 Minus Each Unit Marker Surpassed

Figure 7:
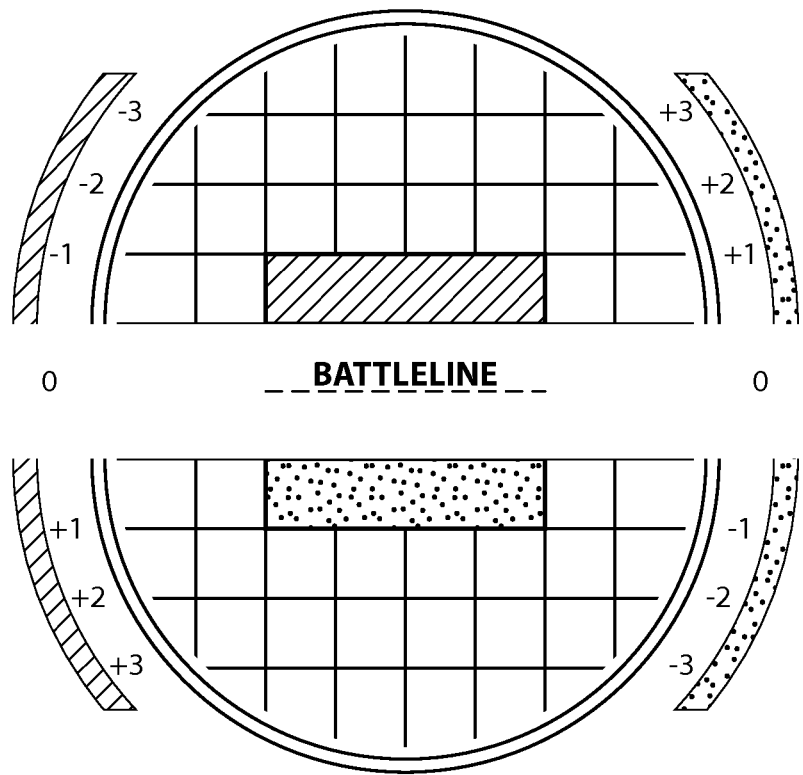
FIG. 7 shows a top view of a culture dish that has been cut along the battle line, for purposes of analysis.
Figure 8:
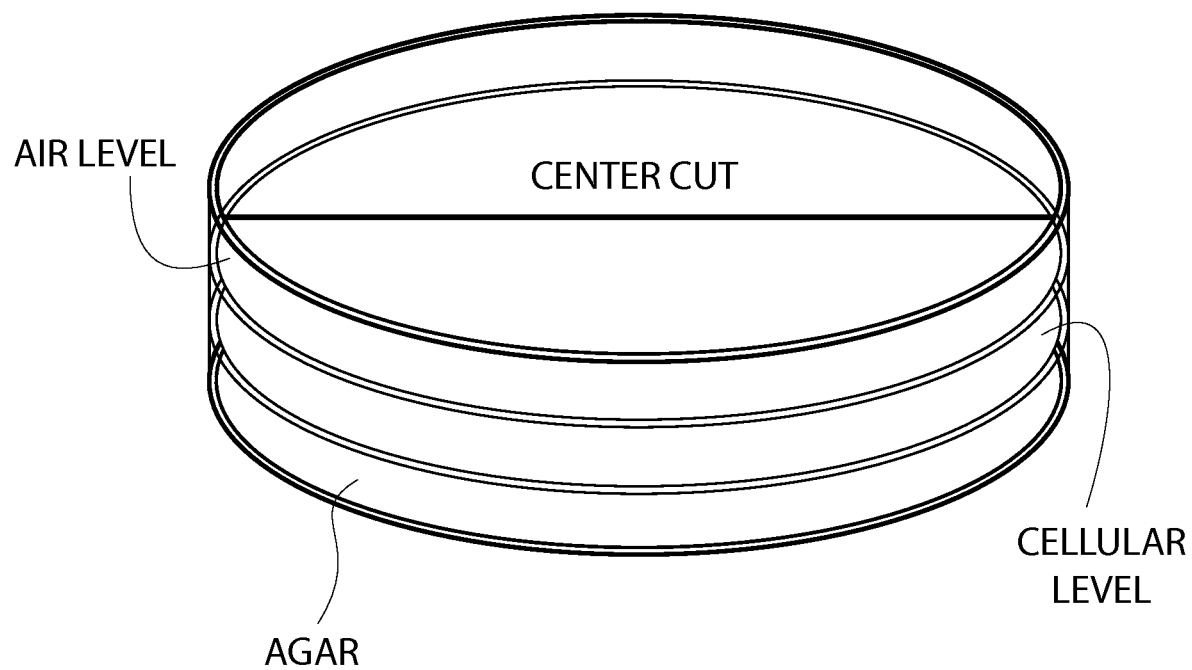
FIG. 8 shows a perspective view of a culture dish that has been cut along the battle line, for purposes of analysis.
Figure 9:
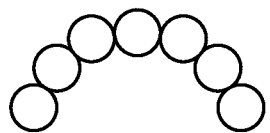
FIG. 9 shows various possible offensive behaviors of a dominant cancer cell line.
Figure 9:
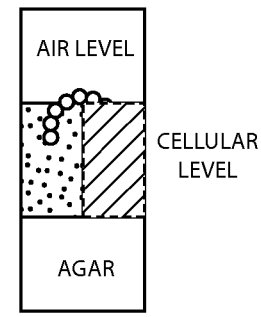
Figure 9:
Figure 9:
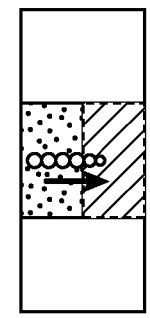
Figure 9:
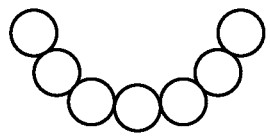
Figure 9:
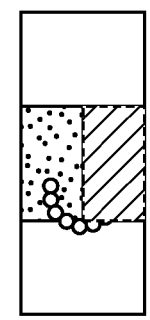
Figure 9:
Figure 9:
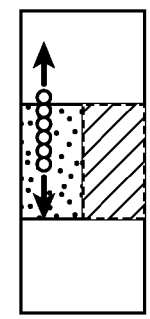
Figure 10:
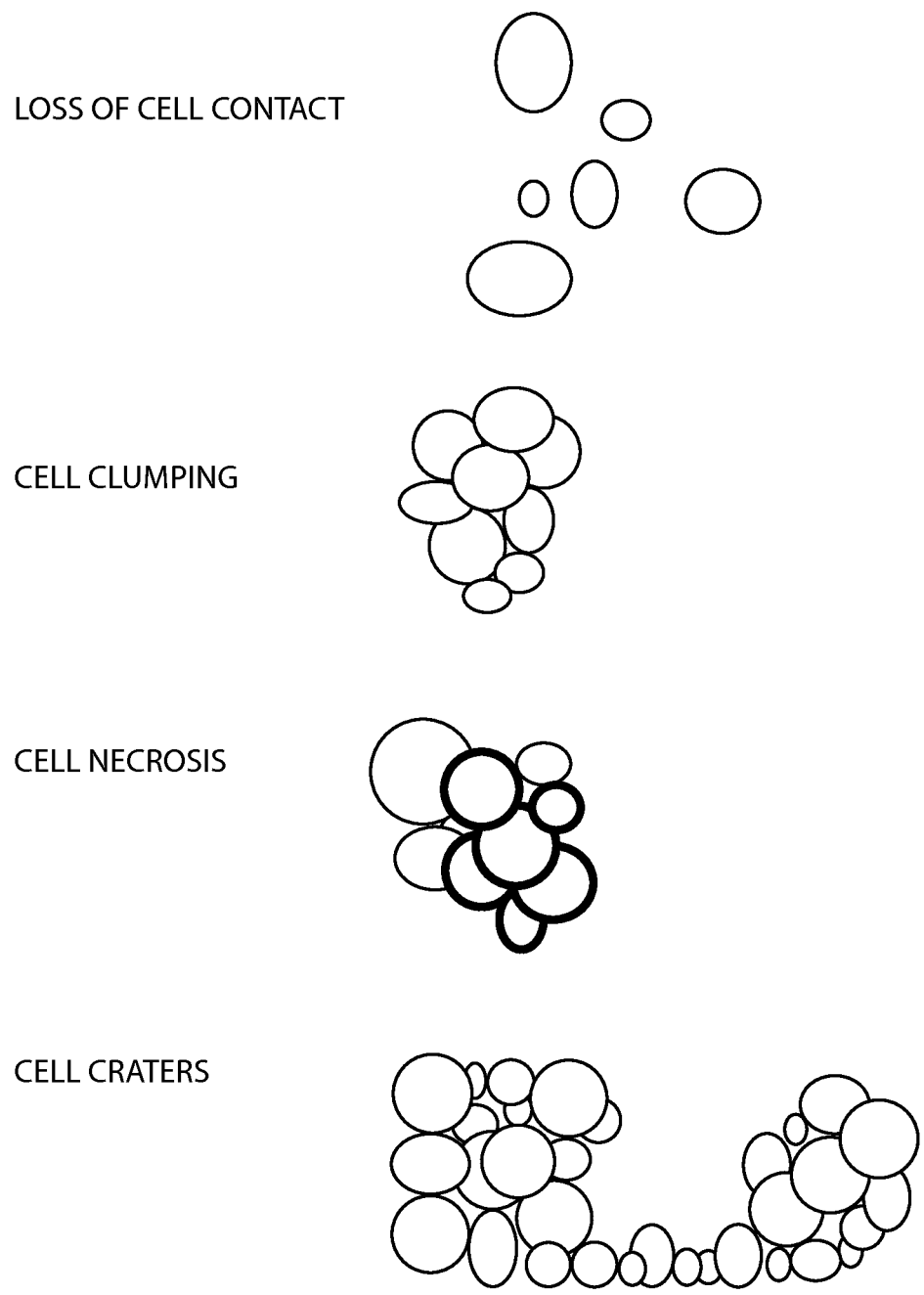
FIG. 10 shows various possible defensive behaviors of a submissive cancer cell line.
Figure 11:
FIG. 11 shows a possible scoring system for target tumors and stock tumors for aggressive behaviors and reciprocally subtracting points for passive and submissive behaviors.

Quantitative scoring and analysis of the two tumor cell populations is facilitated by physically separating the two tumor cell populations and examining each. For example, the contents of each of the 10 battle dishes may be placed on a metal disk and rapidly freezing the disk to −30° C. with liquid nitrogen. The frozen contents of each battle dish are cut with the microtome of a cryostat along the midline and through the battleline of the stock/target tumor confrontation, as shown in FIGS. 7 and 8. The cut section is transferred to a glass slide and the slide is stained, for example, with hematoxylin and eosin. The frozen section is microscopically examined, paying particular attention to movements, migrations, metamorphoses and necrosis. Various types of movement characteristics are possible, as shown in FIGS. 9 and 10. For example, a dominant cell population may bridge over and around, or tunnel under and around, the outside of and into the body of a submissive cell population. A dominant cell population may, alternatively, channel directly through the main body and into the center of a submissive cell population. A dominant cell population may also ladder up or down by expanding upwardly or downwardly more aggressively than the adjacent submissive cell population. Alternatively, some submissive characteristics or "behaviors" may include, for example, loss of cell contact, cell clumping, cell necrosis and cell cratering. Pre-determined points may be awarded to both the target tumor and the stock tumor for aggressive behaviors and reciprocally subtracting points for passive and submissive behaviors. A scoreboard is tabulated with identification of the stock tumor that exhibited the greatest dominance over the target tumor as manifested by the highest point differential between the two, thereby establishing the most superior stock tumor. One example of a possible microscopic scoring system is shown in FIG. 11.

Subsequent experiments may be conducted, re-confronting of the most superior stock tumor with the target tumor by, for example, the process described above—re-plating 100,000 cells of each tumor along the midline of a battle dish containing an enriched growth medium and incubating the dish for 7 days at 3° C. with a humidified atmosphere of 5% $CO_2$. The contents of the incubated dish are then transferred to a 15 cc conical tube where it can be centrifuged, for example, at 1520 rpm for 5 minutes to separate the cellular elements from the proteinatious material and the agar.

The objective of the above cell population "challenge" is to facilitate conditions suitable for the production of cellular components responsible for attacking and killing other cancer cells. Cellular components that are responsible for aggressively attacking and killing other cancer cells in vitro, would be expected to have potential anti-cancer activity in vivo. In order to isolate those cellular components responsible for aggressive behavior of the dominant cell populations, the protein containing layer in the culture dish may be examined by, for example, utilizing gel electrophoresis and highly sensitive biological mass spectrometry to identify any and all polypeptides that are currently identifiable and entering them into an international DNA data base to facilitate future re-identification. A series of these easily identifiable proteins is placed on a compartmentalized eluting disc which when brought into contact with the target tumor culture will elicit either tumorcidal, tumor static or tumor resistive behavior. Recombinant DNA technology is then used to replicate all identifiable proteins to create a purified and safely administrable agent that has already exhibited the in-vitro potential to dominate a target tumor.

Tumor exchanges may be established where cancer treatment centers will have access to a literal supermarket of subcultured stock tumors and secondarily inducted subcultured target tumors to provide a relative ease of access and rapid deployment to the war against cancer. Breeding and training a line of super tumors that can repeatedly and overwhelmingly demonstrate their superiority over a large variety of target tumors. Performance enhancing agents may be developed and deployed, for example, by being adding to a subcultured super tumor to augment its ability to express even more potent tumorcidal agents.

Experimental Results

Cancer cells are unlike normal cells in that they manifest sustained proliferative signaling, evade growth suppressors, resist cell death, and do not manifest inter-cellular contact inhibition. The purpose of this pilot study was to assess the extent of this in tissue culture and to evaluate whether dissimilar tumor types could impede or inhibit the growth and proliferation of target malignant cells upon contact.

Methods: Prospectively, a series of surgically excised and pathologically confirmed malignant tumors were harvested and dissociated from the adherent state into a cell suspension. After the demonstration of adequate cell viability and a 90% dissociation rate, the cancer cells were, using international standards for human cell subculture, deposited into a stock tumor bank. After an aggregate of at least 7 different tumor cell lines were established, the sub-cultured cancer cells were withdrawn from the stock tumor bank and using all possible permutations and combinations were paired with a dissimilar cancer cell sub-culture to produce a total of 21 different tumor pairs, which were then plated on diametrically opposed sections of a gridded petri dish containing an enriched growth medium and incubated for 7 days. All 21 petri dishes were removed from the incubator, opened and examined both visually and microscopically with particular attention to changes in size, color, texture, movements, migrations and metamorphosis. A scoring system was created that awarded points for offensive behaviors and similarly subtracted points for passive and defensive maneuvers.

Results: The points were tallied and arranged in descending order to establish a tumor hierarchy. Ovarian, lymphoma, and breast cancer appeared as the most robust and aggressive, achieving the highest degree of objective infiltration, predominance and destruction of the opposing tumor cell type. Renal and lung cancer demonstrated intermediate performance, with colon and gastric trailing behind.

Conclusion. This pilot experiment has revealed that inter-cellular competition exists between sub-cultured target tumor cells and dissimilar malignant tissue in an in-vitro model. There appear to be numerous mechanisms by which diverse tumor cell types can coexist, predominate or dominate when competing for the same pool of resources.

Prospectively, 20 consecutive and previously untreated, surgically excised tumors were harvested. Nine specimens were determined to be histologically benign and were excluded. The remaining 11 samples were all pathologically confirmed to be malignant, however 4 tumors had to be excluded due to a redundant diagnosis or an inadequate sample size. The group that remained included Table 5, below.

TABLE 5

Selected tumor samples and demographic characteristics.

| | |
|---|---|
| Non Hodkins Lymphoma | 73M |
| Infiltrative Ductal Breast Cancer | 65F |
| Gastric Adenocarcinoma | 53M |
| Squamous Cell Carcinoma of Lung | 61M |
| Renal Cell Carcinoma | 48F |
| Ovarian Serous Cystadenocarcinoma | 52F |
| Colonic Carcinoma | 80M |

Each specimen was visually examined for the location of cancer hotspots likely containing the richest concentration of cancer infiltration. Extreme care was taken to avoid areas of necrosis, stromal tissue, thrombotic material and nests of surrounding normal cells.

These areas were gently probed and the adherent tissue was teased off the body of the hotspots and placed in a culture vessel. The cells were then washed with a balanced salt solution and dissociated with trypsin to produce a cell suspension. A coulter counter was used to confirm a greater than 90% rate of dissociation and cell viability. If either could not be confirmed, then the process would revert back to the first step until both criteria were satisfied.

Once completed, the cell suspension was diluted with McCoys medium 5A supplemented with a 5% fetal calk serum solution to achieve a concentration of 100,000 cells/ml. Next, 10 ml of each tumor cell suspension was sub-cultured on a bed of pre-warmed growth medium and was deposited into an incubated stock tumor bank.

After an aggregate of 7 dissimilar stock tumor sub-cultures were collected, approximately 100,000 cancer cells were withdrawn from each account and paired with all possible combinations of dissimilar tumors to yield a total of 21 different matched tumor pairs.

These were then plated on diametrically opposed sections of a gridded petri dish and incubated at 37 degrees Celsius for 7 days in a humidified atmosphere of 5% $CO_2$ on an enriched growth medium containing chocolate agar. The dishes containing the matched tumor pairs were then opened and examined with particular attention to changes in size, color, texture and motility patterns.

TABLE 6a

| Aggressive Behaviors | |
|---|---|
| A | +4 Plus Each Unit Marker Surpassed |
| B | +3 |
| C | +2 |
| D | +1 |

TABLE 6b

| Passive Behaviors | |
|---|---|
| E | −3 Minus Each Unit Marker Surpassed |
| F | −4 Minus Each Unit Marker Surpassed |

The contents of all 21 separate petri dishes were frozen to −30° C. with liquid nitrogen, cut with the microtome of a cryostat, transferred to a glass slide and stained with hematoxylin and eosin.

Microscopic examination of the frozen section was performed with particular attention to movements across, along, above and below the contact line. Predetermined points were awarded or subtracted to both the target tumor and the stock tumor for aggressive behaviors or passive behaviors, as well as size, color and texture, as described in TABLES 1, 2, 3, 4, 6a, 6b and 7.

TABLE 7

System for scoring microscopic findings
Microscopic Examination

| | | |
|---|---|---|
| 1. Tunneling into the agar below the surface | +1 |
| 2. Channeling into the opposing tumor | +1 |
| 3. Bridging above the opposing tumor | +1 |
| 4. Bridging above with linkage to other bridges | +2 |
| 5. Laddering over the surface | +1 |
| 6. Cratering into the Agar | −3 |
| 7. Budding | +1 |
| 8. Necrotic Debris | −5 |

As shown above in TABLE 7, within the matched pairs, the tumor that scored higher than its counterpart was declared to be the winner. If both scores were equal the match was declared to be a stalemate. The scoreboard was structured in descending order of victories. The engagement between gastric cancer and colon cancer never evolved during the 7 days of incubation so they were both disqualified.

TABLE 8

Overall performance of matched tumor pairs.

| | Wins | Loses | Stalemates |
|---|---|---|---|
| Ovarian | 5 | 1 | 0 |
| Lymphoma | 3 | 1 | 2 |
| Breast | 3 | 2 | 1 |
| Kidney | 3 | 2 | 1 |
| Lung | 2 | 3 | 2 |
| Colon | 1 | 4 | 0 |
| Gastric | 0 | 4 | 1 |

As shown above in TABLE 8, clearly ovarian cancer demonstrated overall dominance with 5 wins and only 1 loss. Lymphoma, Breast and Renal cancer were intermediate in performance, achieving dominance in 50% of the matches. Lung, Colon and Gastric cancer had the poorest performance and were subordinate in the majority of their matches.

There were, however, several major inconsistencies that needed to be reconciled before a definitive statement could be made.

1. Ovarian cancer was subordinate when paired against lymphoma.
2. Lung cancer was dominated by renal cancer to a greater degree than it was by ovarian cancer.
3. Renal cancer was dominated by breast cancer to a greater degree than it was by ovarian cancer.

To address these issues, the matched dissimilar tumor pairs were separated and arranged by the widest margin of dominance exhibited by one tumor cell line over its matched pair (Table 9). An alpha numeric label was assigned to each matched tumor to represent a relative measure of virulence by the dominant tumor over its counterpart. In Table 9, the margin of dominance between matched tumor pairs was quantified with an alpha numeric virulence score, and the pairs rank ordered according to relative potency.

TABLE 9

Widest Margins of Aggressive Behavior for Each Tumor.

| Predominant | Subordinate | Margin | Alpha Numeric Modifier |
|---|---|---|---|
| Lymphoma | Gastric | 26 | LG26 |
| Breast | Kidney | 26 | BK 26 |
| Ovarian | Colon | 23 | OC 23 |
| Lymphoma | Ovarian | 21 | LO 21 |
| Ovarian | Gastric | 20 | OG 20 |
| Kidney | Lung | 18 | KL 18 |
| Lung | Colon | 13 | LC 13 |
| Breast | Colon | 12 | BC 12 |
| Lung | Gastric | 11 | |
| Ovarian | Breast | 9 | |
| Kidney | Colon | 9 | |

This prospective experimental pilot study, conducted at SUNY Downstate Medical Center, was subject to inherent sources of potential bias and a number of limitations. The sample size was small, the observations were limited to gross examination and light microscopy, and assessments were without biochemical assay. While it was not possible to include a control group of non-malignant cells in the study design, the main cohort demonstrated that ovarian, lymphoma and breast cancer cells appeared to be the most robust and aggressive tumor types, and objectively achieved the highest degree of infiltration, predominance, and destruction of the opposing tumor cell type in matched tumor pairs which were incubated and positioned in a square grid petri dish. Renal and lung cancer cells were intermediate in aggressiveness and strength, while colon and gastric cancer cell types performed the poorest, and surprisingly were the most passive.

The tumors that we have presented in this study were all freshly excised stock tumors. Based on our findings, it is anticipated that tumor banks and exchanges will be established and subsequently expanded, populated with simple tumors that are selectively bred and developed into super tumors, based on prior demonstration of potential for dominance. As presented in Table 9, the margin of dominance between matched tumor pairs will be quantified with an alpha numeric virulence score. The objective would be to build upon the alpha numeric modifier to include a species of cancers that will unequivocally and overwhelmingly demonstrate their superiority over the lesser tumor. This will pave the way for creation of a database of ascending alphanumeric modifiers for each individual stock tumor.

Eventually, in clinical practice, freshly diagnosed target tumors may be cross referenced and paired with numbered 'super tumors' in ascending order of potency. A specimen containing a target cancer would be matched, first and foremost, with the super tumor which had been developed and indexed with the greatest alpha numeric modifier. When target tumor tissue is brought into contact with the predominant super tumor, as well as the next 4 or 5 stock tumors according to the virulence scale, the polypeptides and biochemical mediators in the adjacent growth medium will be assayed, identified, and isolated. Utilization of the alpha numeric virulence scoring system will thereby enable the replication, synthesis and selection of the optimal therapeutic intervention required to most efficaciously eradicate a variety of target tumors.

Figure 12:
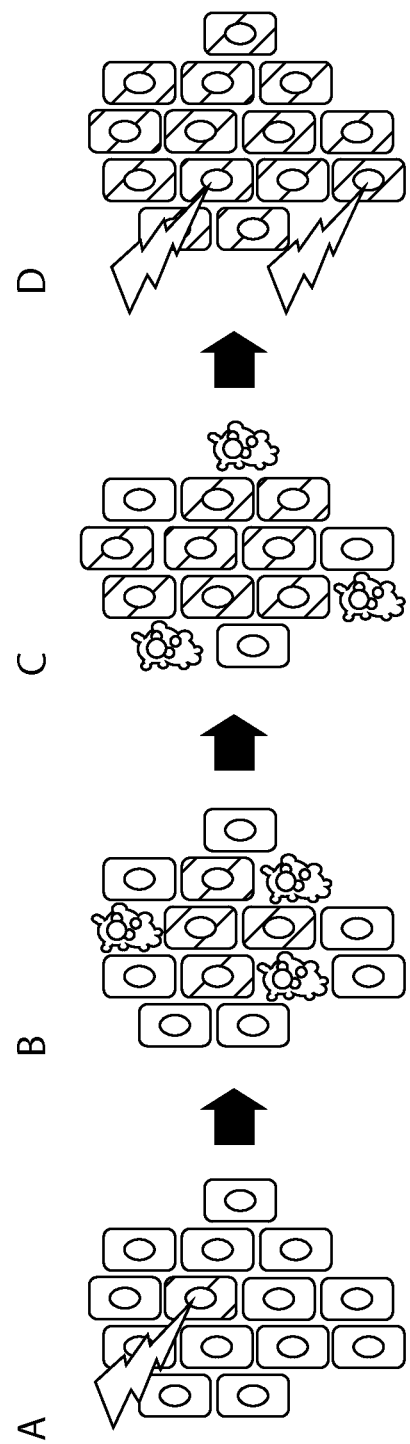
FIG. 12 illustrates how super-competition could contribute to early cancer progression.

In the present study, we have demonstrated that intercellular competition resulted in previously untreated ovarian, lymphoma and breast tumor cells suppressing the growth and proliferation of colon and gastric cancer cells in vitro. Inter-cellular competition seems a plausible physiological mechanism to optimize the quality and survivability of dissimilar tissue types (Moreno 2002). Additionally, genes have been identified that induce a degree of super-competition, a level of inter-cellular competition that is above and beyond the wild-type level (de la Cova 2004, Moreno 2004). The capacity to transform normal cells into super-competitors is thought to result from expression of oncogenes of the myc family. In theory, myc related transformation of normal cells into a super-competitor state could come at the expense of normal and abnormal surrounding tissue in the tumor microenvironment. Although induced apoptosis in adjacent cells could benefit the predominant tumor cells, the total quantity of cell numbers may remain constant [Moreno 2004, Diaz 2005]. This observation has been postulated to be involved in early stages of malignant transformation (FIG. 12), as well as constituting potential mechanism accounting for clinical observations such as the one known as "field cancerization." In field cancerization, a proliferative advantage is associated with a field of cells of monoclonal origin, which expands at the expense of normal and perhaps dissimilar malignant tissue. [Donaldson 2004, Secombe 2004]. As illustrated in FIG. 12, super-competition may contribute to early cancer progression. A mutation of a myc protooncogen could transform a normal epithelial cell into a "super-competitor" (A), able to undergo clonal expansion at the expense of the normal surrounding tissue without any morphological alterations (B and C). Secondary mutations in a super-competitor background could initiate tumor formation (D) (Diaz, 2005)

A number of studies have described mechanisms that could theoretically account for inter-cellular competition and suppression of tumor cell proliferation and replication. A scenario has been described in which cellular competition between malignant and non-malignant cells could be mediated by tumor suppressive miRNAs. As previously reported, miRNAs were found to undergo cellular secretion following exosomal loading (Kosaka 2010, Gibbons 2009, Pegtel 2010). Subsequently, it was found that anti-proliferative miRNAs secretion into the tumor microenvironment by normal cells can impair the proliferation of precancerous cells, whereas cells having undergone malignant transformation may circumvent this inhibitory mechanism, resulting in carcinogenic growth. Therefore, tumor cells may need to overcome the homeostatic mechanism of tumorsuppressive miRNAs secreted into the tumor microenvironment (Kosaka 2012).

These phenomena may explain the observation that intercellular competition and emergence of predominant tumor cell types occurs in dissimilar subcultured malignant tissue, perhaps due to the same secretory miRNAs mechanisms, or a variety of secreted chemokines, cytokines, growth factors, mitogens. There appear to be numerous mechanisms by which diverse tumor cell types can coexist, predominate or dominate when competing for the same pool of resources.

Ultimately, it is contemplated that tumor exchanges may be developed wherein libraries of subcultured stock and target tumor tissue are established to enable further research into the identification of mechanisms and mediators of inter-cellular neoplastic competition, inhibition, and predominance. Clearly, the focus of attention and epicenter of future research will necessarily be the 'battlefields and the surrounding bathwaters' where the targeted tumors were overwhelmed. Analysis of the "tumor microenvironment" and potential or hypothetical proteinaceous and polypeptide materiasl, e.g, cytokines, interleukins, nucleic acids and biochemical mediators, will yield a treasure trove of new and relevant data.

Incorporation of subcultured stock and target tumor tissue into xenograft and tumorgraft murine models will enable identification of tumoristatic and tumoricidal agents in the in-vivo tumor microenvironment. Additionally, the utilization of xenograft and tumorgraft panels will enable response correlation between human and preclinical mouse models, enabling the establishment of an integrated database of tumor-drug response data and biomarkers. This will facilitate the pre-clinical determination of treatment impact on clinical outcomes, such as progression-free and overall survival (Rubio-Viqueira 2006).

Progressing into the clinical testing phase, the use of genomics, proteomics, and ultimately, systems biology in conjunction with preclinical and clinical studies will help to establish new biomarkers and targeted therapies. Finally, the application of advanced data analytics, information technology, and bioinformatics will facilitate development of public and private databases as repositories for this information. Once having undergone rigorous analytical validation and clinical evaluation, clinicians involved in early-phase clinical studies will be able to use these novel biomarkers and directed treatment options for diagnosis, treatment, and patient monitoring. This can be expected to constitute a major contribution to the field of clinical cancer research, enable successful application of the data to medical practice, and to greatly improve the personalized therapeutic options available for cancer patients.

This pilot experiment has revealed that inter-cellular competition exists between previously untreated, subcultured target tumor cells and dissimilar malignant tissue in an in-vitro model. To the best of our knowledge, intercellular competition and unilateral dominance of select cancer tissue types over other malignant subtypes has not previously been reported in the literature. Further studies are needed to validate these findings in vitro and in-vivo.

There is thus disclosed an improved system and method for detecting anti-cancer compounds. It will be appreciated that numerous changes may be made to the present invention without departing from the scope of the claims.

REFERENCES

Parker, R., (1950) Methods of tissue culture. Paul B. Hoeber, Inc. New York, second edition, Scherer, W F., Stverton, J T., Gey, G O. Studies on the propagation of in-vitro poliomyelitis virus. Viral multiplication in a stable strain of human malignant epithelial cells (strain HeLa) derived from an epidermoid carcinoma of the cervix (1953). Journal of Exploratory Medicine, May; 97(5) 695-710.

Abercrombie, M. (1979) Contact Inhibition and Malignancy. Nature, Vol. 281, 259-262.

Earle, W. R., et al. (1954) The growth of pure strain L-cells in fluid-suspension cultures. Journal of the National Cancer Institute, Vol. 14: 1159-1171.

Cell and Tissue Culture (1975) John Paul, 5th edition, Churchill Livangstone Edinburgh.

Kuchler, R. and Merchant, D. (1958) Growth of tissue cells in suspension. University of Michigan Medical Bulletin Vol. 24: 200-212.

Harvey, A. M. (1975) Johns Hopkins—the birthplace of tissue culture: the story of Ross G. Harrison, Warren Y. Lewis and George O. Gey. Johns Hopkins Medical Journal 136(3): 142-149.

Diaz B, Moreno E. The competitive nature of cells. Exp Cell Res. 2005 Jun. 10; 306(2):317-22. Epub 2005 Apr. 18.

de la Cova, M. Abril, P. Bellosta, P. Gallant, L. A. Johnston. Drosophila myc regulates organ size by inducing cell competition, Cell 117 (1) (2004 Apr. 2) 107-116.

Hanahan, D., and Weinberg, R. A. (2000). The hallmarks of cancer. Cell 100, 57-70.

Hanahan D, Weinberg R A. Hallmarks of cancer: the next generation. Cell. 2011 Mar. 4; 144(5):646-74.

Gibbings, D J. Ciaudo, C, Erhardt, M, and Voinnet, O. (2009) Nat Cell Biol 11(9), 1143-1149

Kandasamy K, Mohan S S, Raju R et al. NetPath: a public resource of curated signal transduction pathways. Genome Biol. 2010 Jan. 12; 11(1):R3

Kosaka N, Iguchi H, Yoshioka Y, Takeshita F, Matsuki Y, Ochiya T. Secretory mechanisms and intercellular transfer of microRNAs in living cells. J Biol Chem. 2010 Jun. 4; 285(23):17442-52. doi: 10.1074/jbc.M110.107821. Epub 2010 Mar. 30.

Kosaka N1, Iguchi H, Yoshioka Y, Hagiwara K, Takeshita F, Ochiya T. Competitive interactions of cancer cells and normal cells via secretory microRNAs. J Biol Chem. 2012 Jan. 6; 287(2):1397-405. doi: 0.1074/jbc.M111.2 88662

Moreno E, Basler K, Morata G. Cells compete for decapentaplegic survival factor to prevent apoptosis in Drosophila wing development, Nature 416 (6882) (2002 Apr. 18) 755-759.

Moreno E, Basler K. dMyc transforms cells into supercompetitors, Cell 117 (1) (2004 Apr. 2) 117-129.

Pegtel, D. M., Cosmopoulos, K., Thorley-Lawson, D. A., van Eijndhoven, M. A., Hopmans, E. S., Lindenberg, J. L., de Gruijl, T. D., Wurdinger, T., and Middeldorp, J. M. (2010) Proc Natl Acad Sci USA 107(14), 6328-6333

Purves D. Neuronal competition, Nature 287 (5783) (1980 Oct. 16) 585-586.

Weinberg R A. Biology of Cancer. Garland Science, Taylor & Francis Group. May 2006.

Secombe J, Pierce S B, Eisenman R N. Myc: a weapon of mass destruction. Cell. 2004 Apr. 16; 117(2):153-6. Review.

Donaldson T D1, Duronio R J. Cancer cell biology: Myc wins the competition. Curr Biol. 2004 Jun. 8; 14(11): R425-7.

Rubio-Viqueira B1, Jimeno A, et al. An in vivo platform for translational drug development in pancreatic cancer. Clin Cancer Res. 2006 Aug. 1; 12(15):4652-61.

The invention claimed is:

1. A method for identifying expansion in area of a colony of first malignant cancer cells with commensurate regression in area of a different colony of second malignant cancer cells in the same area as the expansion of the colony of first malignant cancer cells in an adjacent confrontation, comprising:

plating on a culture plate in a growth medium a colony of first naturally occurring malignant cancer cells and a colony of second naturally occurring malignant cancer cells on directly opposite sides of a midline adjacent one another, wherein the first naturally occurring malignant cancer cells comprise a first type of cancer cell derived from a single malignant cancer cell of the first type of cancer cell and wherein the second naturally occurring malignant cancer cells comprise a second type of cancer cell derived from a single malignant cancer cell of the second type of cancer cell, wherein the first type of cancer cell and the second type of cancer cell are of different cancer types;

culturing the colony of first naturally occurring malignant cancer cells and the colony of second naturally occurring malignant cancer cells under conditions sufficient to promote growth of the cancer cells;

measuring the area of expansion of the colony of first naturally occurring malignant cancer cells across the midline into the area of the colony of second naturally occurring malignant cancer cells that is accompanied by regression of the colony of second naturally occurring malignant cancer cells from the midline commensurate with the area of expansion of the colony of first naturally occurring malignant cancer cells;

plating on a culture plate in a growth medium a colony of third naturally occurring malignant cancer cells and a colony of fourth naturally occurring malignant cancer cells on directly opposite sides of a midline adjacent one another, wherein the colony of third naturally occurring malignant cancer cells comprises a third type of cancer cell derived from a single malignant cancer cell of the third type of cancer cell and wherein the colony of fourth naturally occurring malignant cancer cells comprises a fourth type of cancer cell derived from a single malignant cancer cell of the fourth type of cancer cell, wherein the third type of cancer cell and the fourth type of cancer cell are of different cancer types;

culturing the colony of third naturally occurring malignant cancer cells and the colony of fourth naturally occurring malignant cancer cells under conditions sufficient to promote growth of the cancer cells;

measuring the area of expansion of the colony of third naturally occurring malignant cancer cells across the midline into the area of the colony of fourth naturally occurring malignant cancer cells that is accompanied by regression of the colony of fourth naturally occurring malignant cancer cells from the midline commensurate with the area of expansion of the colony of third naturally occurring malignant cancer cells;

identifying a first dominant cancer cell from the first naturally occurring malignant cancer cells and the second naturally occurring malignant cancer cells;

identifying a second dominant cancer cell from the third naturally occurring malignant cancer cells and the fourth naturally occurring malignant cancer cells; and adjacently confronting the first dominant cancer cells and the second dominant cancer cells by plating on a culture plate in a growth medium a first dominant colony of the first dominant cancer cells and a second dominant colony of the second dominant cancer cells on directly opposite sides of a midline adjacent one another; culturing the first dominant colony and the second dominant colony under conditions sufficient to promote growth of the first dominant cancer cells and the second dominant cancer cells; and measuring the area of expansion of one of the first dominant colony and the second dominant colony across the midline that is accompanied by commensurate regression of the other of the first dominant colony and the second dominant colony from the midline.

2. The method of claim 1, wherein the colony of first naturally occurring malignant cancer cells and the colony of second naturally occurring malignant cancer cells plated each have about an equal number of cancer cells.

3. The method of claim 1, wherein the colony of first naturally occurring malignant cancer cells and the colony of second naturally occurring malignant cancer cells plated each have about $10^4$ cells or greater.

4. The method of claim 1, wherein the colony of first naturally occurring malignant cancer cells and the colony of second naturally occurring malignant cancer cells plated each have about $10^5$ cells or greater.

5. The method of claim 1, wherein the colony of first naturally occurring malignant cancer cells and the colony of second naturally occurring malignant cancer cells plated each cover an area that is about equal.

6. The method of claim 1, further comprising the step of subculturing and expanding the colony of first naturally occurring malignant cancer cells that expands into the area of the colony of second naturally occurring malignant cancer cells.

7. The method of claim 1, wherein the culture plate comprises unit markers for scoring the area of expansion and area of decrease of the colony of first malignant cancer cells and the colony of second malignant cancer cells.

8. The method of claim 1, wherein the colony of first malignant cancer cells and the colony of second malignant cancer cells are plated at a density of about $10^6$ cells/mL or greater.

9. A method for confronting a colony of malignant cancer cells with a different colony of malignant cancer cells, comprising:

plating on a culture plate in a growth medium a colony of first naturally occurring malignant cancer cells and a colony of second naturally occurring malignant cancer cells on directly opposite sides of a midline adjacent one another, wherein the colony of first naturally occurring malignant cancer cells comprise a first type of cancer cell derived from a single malignant cancer cell of a first type of cancer and wherein the colony of second naturally occurring malignant cancer cells comprise a second type of cancer cell derived from a single malignant cancer cell of a second type of cancer, wherein the first type of cancer cell and the second type of cancer cell are of different cancer types;

culturing the colony of first naturally occurring malignant cancer cells and the colony of second naturally occurring malignant cancer cells under conditions sufficient to promote growth of the cancer cells;

measuring an area of expansion of the colony of first naturally occurring malignant cancer cells across the midline into an area of the colony of second naturally occurring malignant cancer cells that is accompanied by regression of the colony of second naturally occurring malignant cancer cells from the midline commensurate with the area of expansion of the colony of first naturally occurring malignant cancer cells;

plating on a culture plate in a growth medium a colony of third naturally occurring malignant cancer cells and a colony of fourth naturally occurring malignant cancer cells on directly opposite sides of a midline adjacent one another, wherein the colony of third naturally occurring malignant cancer cells comprises a third type of cancer cell derived from a naturally occurring third tumor and wherein the colony of fourth naturally occurring malignant cancer cells comprises a fourth type of cancer cell derived from a naturally occurring fourth tumor, and wherein the third type of cancer cell and the fourth type of cancer cell are of different cancer types;

culturing the colony of third naturally occurring malignant cancer cells and the colony of fourth naturally occurring malignant cancer cells under conditions sufficient to promote growth of the cancer cells;

measuring the area of expansion of the colony of third naturally occurring malignant cancer cells across the midline into the area of the colony of fourth naturally occurring malignant cancer cells that is accompanied by regression of the colony of fourth naturally occurring malignant cancer cells from the midline commensurate with the area of expansion of the colony of third naturally occurring malignant cancer cells; and adjacently confronting the first type of cancer cell and the third type of cancer cell by plating on a culture plate in a growth medium the colony of first naturally occurring malignant cancer cells and the colony of third naturally occurring malignant cancer cells on directly opposite sides of a midline adjacent one another; culturing the colony of first naturally occurring malignant cancer cells and the colony of third naturally occurring malignant cancer cells under conditions sufficient to promote growth of the cancer cells; and measuring the area of expansion of the colony of the first naturally occurring malignant cancer cells across the midline into the area of the colony of third naturally occurring malignant cancer cells that is accompanied by regression of the colony of third naturally occurring malignant cancer cells from the midline commensurate with the area of expansion of the colony first naturally occurring malignant cancer cells.

* * * * *